(12) United States Patent
Cubon

(10) Patent No.: US 10,842,667 B2
(45) Date of Patent: Nov. 24, 2020

(54) SELF-REGULATING HEATER

(71) Applicant: HORIZONS INCORPORATED, Cleveland, OH (US)

(72) Inventor: Michael M. Cubon, Park Ridge, IL (US)

(73) Assignee: TRAMEC TERMICO TECHNOLOGIES, L.L.C., Iola, KS (US)

( * ) Notice: Subject to any disclaimer, the term of this patent is extended or adjusted under 35 U.S.C. 154(b) by 304 days.

(21) Appl. No.: 15/435,954

(22) Filed: Feb. 17, 2017

(65) Prior Publication Data

US 2017/0231811 A1    Aug. 17, 2017

Related U.S. Application Data

(60) Provisional application No. 62/320,770, filed on Apr. 11, 2016, provisional application No. 62/308,326, filed on Mar. 15, 2016, provisional application No. 62/296,427, filed on Feb. 27, 2016.

(51) Int. Cl.
*A61F 7/02* (2006.01)
*A61F 7/00* (2006.01)

(52) U.S. Cl.
CPC .............. *A61F 7/02* (2013.01); *A61F 7/007* (2013.01); *A61F 7/0053* (2013.01); *A61F 7/0097* (2013.01); *A61F 2007/0011* (2013.01); *A61F 2007/0036* (2013.01); *A61F 2007/0071* (2013.01); *A61F 2007/0074* (2013.01); *A61F 2007/0226* (2013.01); *A61F 2007/0233* (2013.01)

(58) Field of Classification Search
CPC .... A61F 7/007; A61F 7/02; A61F 7/08; A61F 2007/0071; A61F 2007/0244; A41D 13/002; A41D 13/005; A41D 13/0051; A41D 13/0058
See application file for complete search history.

(56) References Cited

U.S. PATENT DOCUMENTS

| 6,066,164 | A | * | 5/2000 | Macher | ............ | A41D 19/01535 |
|  |  |  |  |  |  | 219/528 |
| 6,532,824 | B1 | * | 3/2003 | Ueno | ...................... | G01L 1/142 |
|  |  |  |  |  |  | 73/780 |
| 8,008,607 | B2 | * | 8/2011 | Ptasienski | ................ | H05B 3/26 |
|  |  |  |  |  |  | 219/212 |

(Continued)

*Primary Examiner* — Kaitlyn E Smith
(74) *Attorney, Agent, or Firm* — Tarolli, Sundheim, Covell & Tummino LLP

(57) ABSTRACT

The present invention is directed to a self regulating heater including a first layer made of a thin and flexible electrically insulating material. A second electrically conductive layer includes first and second buses spaced from each other. A third resistive layer electrically connects the first and second buses. The third layer has a higher electrical resistance than the second layer. The third layer experiences a positive temperature coefficient (PTC) effect when heated. A fourth interface layer directly connected to at least one of the second electrically conductive layer and the third resistive layer directly engages skin of a patient when the heater is attached to the patient. A combined thickness of the first layer, the second conductive layer, the third resistive layer and the fourth layer may be between 5 mil and 20 mil.

15 Claims, 4 Drawing Sheets

(56) References Cited

U.S. PATENT DOCUMENTS

| | | | | |
|---|---|---|---|---|
| 8,702,164 B2* | 4/2014 | Lazanja | ............... | B60N 2/5685 297/180.12 |
| 8,736,000 B1* | 5/2014 | Manginell | ............ | G01N 27/221 257/215 |
| 8,901,464 B2* | 12/2014 | Ptasienski | ................ | H05B 3/26 118/728 |
| 9,420,640 B2* | 8/2016 | Li | ............................. | H05B 3/34 |
| 2004/0065651 A1* | 4/2004 | Voeltzel | ............. | B32B 17/10036 219/203 |
| 2006/0010902 A1* | 1/2006 | Trinh | ....................... | A61F 7/02 62/457.2 |
| 2006/0054616 A1* | 3/2006 | Ptasienski | ................ | H05B 3/20 219/543 |
| 2007/0023419 A1* | 2/2007 | Ptasienski | ................ | H05B 3/26 219/543 |
| 2008/0041843 A1* | 2/2008 | Bower | ................... | F16K 27/003 219/544 |
| 2009/0032523 A1* | 2/2009 | Youngblood | .......... | H05B 3/342 219/528 |
| 2010/0057168 A1* | 3/2010 | Slade | ..................... | A61F 7/007 607/99 |
| 2010/0108661 A1* | 5/2010 | Vontell | .................... | H05B 3/34 219/477 |
| 2010/0176118 A1* | 7/2010 | Lee | .......................... | H05B 3/34 219/549 |
| 2010/0206308 A1* | 8/2010 | Klasek | .............. | A61M 16/0066 128/203.27 |
| 2010/0219664 A1* | 9/2010 | Howick | ............... | B60N 2/5678 297/180.12 |
| 2011/0290775 A1* | 12/2011 | Cubon | ................... | B60N 2/002 219/209 |
| 2012/0113196 A1* | 5/2012 | Alavizadeh | .......... | B41J 2/17593 347/88 |
| 2012/0225424 A1* | 9/2012 | Abassi | ................... | C12M 35/02 435/5 |
| 2013/0068754 A1* | 3/2013 | Ptasienski | ................ | H05B 3/26 219/541 |
| 2013/0172829 A1* | 7/2013 | Badawi | ................. | A61F 9/0008 604/294 |
| 2013/0239966 A1* | 9/2013 | Klasek | .............. | A61M 16/0066 128/203.27 |
| 2013/0327762 A1* | 12/2013 | Ptasienski | ................ | H05B 3/02 219/553 |
| 2016/0100977 A1* | 4/2016 | Lee | .......................... | A61F 7/007 607/109 |
| 2016/0132146 A1* | 5/2016 | Cok | .......................... | G06F 3/044 345/174 |
| 2016/0299543 A1* | 10/2016 | Brooks | .................. | H05B 3/145 |
| 2017/0276711 A1* | 9/2017 | Pak | .......................... | G01D 5/24 |

* cited by examiner

SELF-REGULATING HEATER

RELATED APPLICATIONS

This application claims priority from U.S. Provisional Application Ser. No. 62/296,427, filed Feb. 17, 2016, U.S. Provisional Application Ser. No. 62/308,326, filed Mar. 15, 2016, and U.S. Provisional Application Ser. No. 62/320,770, filed Apr. 11, 2016, the subject matter of which are incorporated herein by reference in their entirety.

FIELD OF THE INVENTION

The present invention relates to a self-regulating heater and, more specifically, to a polymeric positive temperature coefficient (PTC) heater.

BACKGROUND OF THE INVENTION

It is commonly established that patients undergoing surgery and under the influence of anesthesia are unable to regulate their core body temperature. There is a threat to the patients of heat loss, and possibly hypothermia if core body temperature cannot be maintained. Hypothermia can pose an increased risk of surgical infection and other post-operative complications, such as impaired drug metabolism and immune functions.

A number of known systems are designed to maintain normothermia. All of these systems have a failure mode (or design features) which could be hazardous to the patient.

Forced-air warming systems that are known are noisy, bulky, and can struggle to quickly and effectively warm the patient. Also, the forced air can stir up airborne contaminants from surgical room floors. In addition, inadvertent contact with the hosing mechanisms poses a threat of burning a patient. The air leaving a forced air system loses heat after leaving the hose and the temperature of the air leaving the hose can be as high as 45° C. If this air blows directly onto the patient's skin prior to connection to a blanket, another potential threat of burning the patient can occur.

Other patient warming systems use a fixed resistance heater which requires a sensing device to control the temperature. In the event that this device malfunctions or the temperature is allowed to increase in other areas of the heater outside of the sensor, the heating device can cause a hazardous condition to the patient.

The assembly of these devises can be cumbersome and involve wrapping the patient in a blanket.

SUMMARY OF THE INVENTION

The present invention is directed to a self regulating heater including a first layer made of a thin and flexible electrically insulating material. A second electrically conductive layer includes first and second buses spaced from each other. A third resistive layer electrically connects the first and second buses. The third layer has a higher electrical resistance than the second layer. The third layer experiences a positive temperature coefficient (PTC) effect when heated. A fourth interface layer directly connected to at least one of the second electrically conductive layer and the third resistive layer directly engages skin of a patient when the heater is attached to the patient.

In another aspect of the present invention a self regulating heater includes a first layer made of an electrically insulating material. The first layer is thin and flexible. A second electrically conductive layer includes first and second buses spaced from each other. A third resistive layer electrically connects the first and second buses. The third layer has a higher electrical resistance than the second layer. The third layer experiences a positive temperature coefficient (PTC) effect when heated. The heater also includes a fourth interface layer directly connected to at least one of the second electrically conductive layer and the third resistive layer. A combined thickness of the first layer, the second conductive layer, the third resistive layer and the fourth layer is between 5 mil and 20 mil.

The self regulating heater may have at most a 4° F. difference across the surface of the heater. The fourth layer may be an adhesive that completely seals the heater and adheres the heater directly to skin of a patient. The heater conforms to a body part of the patient when adhered directly to the skin of the patient.

BRIEF DESCRIPTION OF THE DRAWINGS

The foregoing and other features and advantages of the present invention will become apparent to one skilled in the art upon consideration of the following description of the invention and the accompanying drawings, in which.

DETAILED DESCRIPTION

Figure 1:
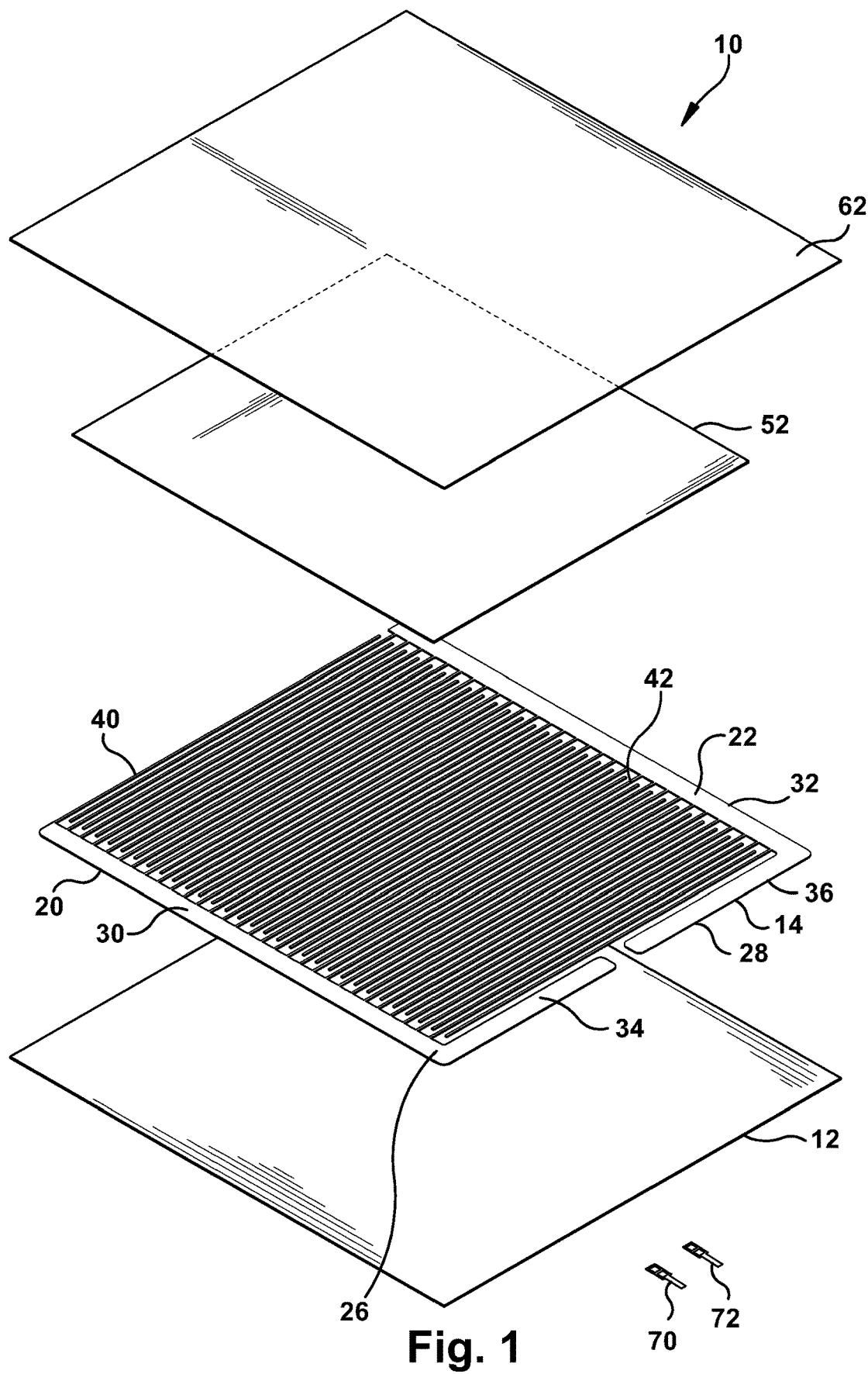
FIG. 1 is an exploded view of a first embodiment of a self-regulating heater constructed in accordance with the present invention.

FIG. 1 illustrates a self-regulating heater 10 made in accordance with the present invention. The heater 10 includes a first layer or substrate 12 made of an electrically insulating material. The first layer 12 may be relatively thin and flexible. Preferably, the first layer 12 is a film substrate made of any desired electrically insulating material such as Mylar.

A second or electrically conductive layer 14 made of an electrically conductive material is connected to the first layer 12 and engages the first layer. The second layer 14 may be made of a flexible polymeric ink. The second layer 14 may be connected to the first layer 12 in any desired manner and is preferably screen printed on the first layer. The second layer 14 may be connected to the first layer 12 by close tolerance screen printing, digital printing, inkjet printing, flexographic printing, or gravure printing.

The second layer 14 includes at least two buses 20 and 22 spaced from each other. The patterns of the buses 20, 22 determine the watt density of the heater 10. The buses 20 and 22 may include bases 26 and 28 having a relatively large width. The bases 26 and 28 may include first portions 30 and 32 extending generally parallel to each other. Although the first portions 30 and 32 are shown extending in a straight line, it is contemplated that the first portions may extend in any desired direction.

The bases 26 and 28 may include second portions 34 and 36 extending toward each other from the first portions 30 and 32. The second portions 34 and 36 may extend perpendicular to the first portions 30 and 32. Although the second portions 34 and 36 are described as extending perpendicular to the first portions 30, 32, it is contemplated that the second portions 34 and 36 may extend in any desired direction.

The buses 20 and 22 may include finger portions 40 and 42 extending from the first portions 30 and 32. The finger portions 40 and 42 may extend generally between each other and parallel to each other and the second portions 34 and 36 of the bases 26 and 28. The finger portions 40 and 42 may have a width substantially smaller than the width of the bases 26 and 28. Although the finger portions 40, 42 are described as extending generally parallel to the second portions 34, 36, it is contemplated that the finger portions may extend in any desired direction. Although the buses 20, 22 are described as having a specific shape, it is contemplated that the buses 20, 22 may have any desired shape.

A third or resistive layer 52 that experiences a positive temperature coefficient (PTC) effect when heated is connected to the second or conductive layer 14. The third layer 52 engages the second layer 14. The third layer 52 may be connected to the second layer 14 in any desired manner and is preferably screen printed on the second layer. The third layer 52 is connected to the second layer 14 so that the second layer is between the third layer and the first layer 12. The third layer 52 electrically connects the buses 20 and 22 of the second layer 14. The third layer 52 has a higher electrical resistance than the second layer 14. The third layer 52 generates heat when a voltage is applied across the buses 20, 22.

The third or resistive layer 52 includes a conductive carbon black filler material dispersed in a polymer that has a crystalline structure. The crystalline structure densely packs the carbon particles into a crystalline boundary so the carbon particles are close enough together to allow electrical current to flow through the polymer insulator via these carbon "chains" between the first and second buses 20 and 22. When the polymer is at normal room temperature, there are numerous carbon chains forming conductive paths through the material. Heat is produced when current flows through the polymeric device. Heating causes the temperature of the polymer to rise. As the heating continues, the temperature of the material continues to rise until it exceeds a phase transformation temperature. As the material passes through the phase transformation temperature, the densely packed crystalline polymer matrix changes to an amorphous structure. The phase change is accompanied by an expansion of the polymer. As the conductive particles move apart from each other, most of them no longer conduct current and the resistance of the heater 10 increases sharply. The heater 10 will reach a designed steady state temperature and will draw reduced amperage to maintain the steady state temperature. The heater 10 will stay "warm", remaining in this high resistance state as long as the power is applied. Removing the power source will reverse the phase transformation and allow the carbon chains to re-form as the polymer re-crystallizes. The heater resistance returns to its original value.

A fourth or interface layer 62 is directly connected to the third layer 52 so that the fourth layer engages the third layer. The fourth layer 62 may be an adhesive or film that completely seals the heater 10. The fourth layer 62 may directly engage the skin of a patient to attach the heater 10 to the skin. The fourth layer 62 can be a double sided adhesive and allow for the heater 10 to be assembled directly to a patient or to a member that is assembled to the patient. The fourth layer 62 may be attached to any desired material, such as foam and/or fabric. It is contemplated that the interface layer 62 may be made of a hypoallergenic material to reduce the chance for any skin reaction when the interface layer 62 engages the skin of a patient. The interface layer 62 can be attached to a thermally conductive foam material, or an enclosure, or wearable fabric.

A first terminal 70 is connected to the second portion 34 of the base 26. A second terminal 72 is connected to the second portion 36 of the base 28. The terminals 70, 72 may be connected to the bases 26, 28 in any desired manner, such as riveting or crimping. The terminals 70, 72 connect the heater 10 to a voltage supply. The fourth layer 62 may be applied after the terminals 70, 72 are connected to the bases 26, 28 or before the terminals 70, 72 are connected. If the terminals 70, 72 are connected after the fourth layer 62 is applied, openings for crimping of the terminals may be provided in the fourth layer. The terminal connections may then be sealed with a UV encapsulating material.

The heater 10 may be placed directly on the skin of a patient to provide localized heating to a desired temperature. Applying the heater 10 directly to the skin eliminates heat variability associated with interface layers of known devices which prohibits the even flow of heat to the patient. The heater 10 includes a self-regulating PTC with the interface layer 62 that directly engages the skin. The self-regulating heater 10 may be connected to another device, such as a sleeve, sock, or a glove that the patient can wear. The self-regulating heater 10 may be attached to a shirt, pants, hat, scarf, blanket, boot or any other wearable device. The self-regulating heater 10 may be connected to an operating table, examination table (underbody heating) or chair, such as a chemotherapy chair. The heater 10 can also be combined with other medical devices such as monitors and sensors. The heater 10 may be combined with diagnostic sensors such as an EKG test probe or blood pressure probe.

The heater 10 conforms to body parts of a patient because the thickness is controlled. The combined thickness of the layers 12, 14, 52 and 62 may be between 5 mil and 20 mil. The heater 10 is very flexible and may be folded upon itself due to the thickness. The heater 10 may have many different configurations that can include variable watt densities and unlimited shapes and sizes that can provide self-regulating heat. The heater 10 may include slots and holes that allow the heater to be wrapped around contours of the body as well as conform to bending of joints. The heater 10 may have a shape that corresponds to the shape of a body part, such as a hand, foot, eye socket or ear.

The design flexibility of the heater 10 allows for a myriad of shapes and sizes to keep the temperature difference across the heater 10 as low as possible and at most 4° F. It is also contemplated that The fingers 40, 42 and bases 26, 28 may be located closer to each other in predetermined areas of the heater 10 to increase the watt density of the heater in the predetermined areas. For example, the heater 10 may have the shape of a hand with a palm engaging portion and finger engaging portions. The fingers 40, 42 and bases 26, 28 of the buses 20, 22 located in the finger engaging portions of the heater 10 may be spaced from each other a smaller distance that the fingers and bases located in the palm engaging portion of the heater. Therefore, the watt density of the heater 10 in the finger engaging portions would be greater than the watt density of the heater in the palm engaging portion and the finger engaging portions would have a higher steady state temperature than the palm engaging portion.

The process of forming the heater 10 includes close-tolerance screen printing in a controlled environment. The process for forming the heater 10 also includes laminating and curing processes that completely stabilize the part.

Figure 2:
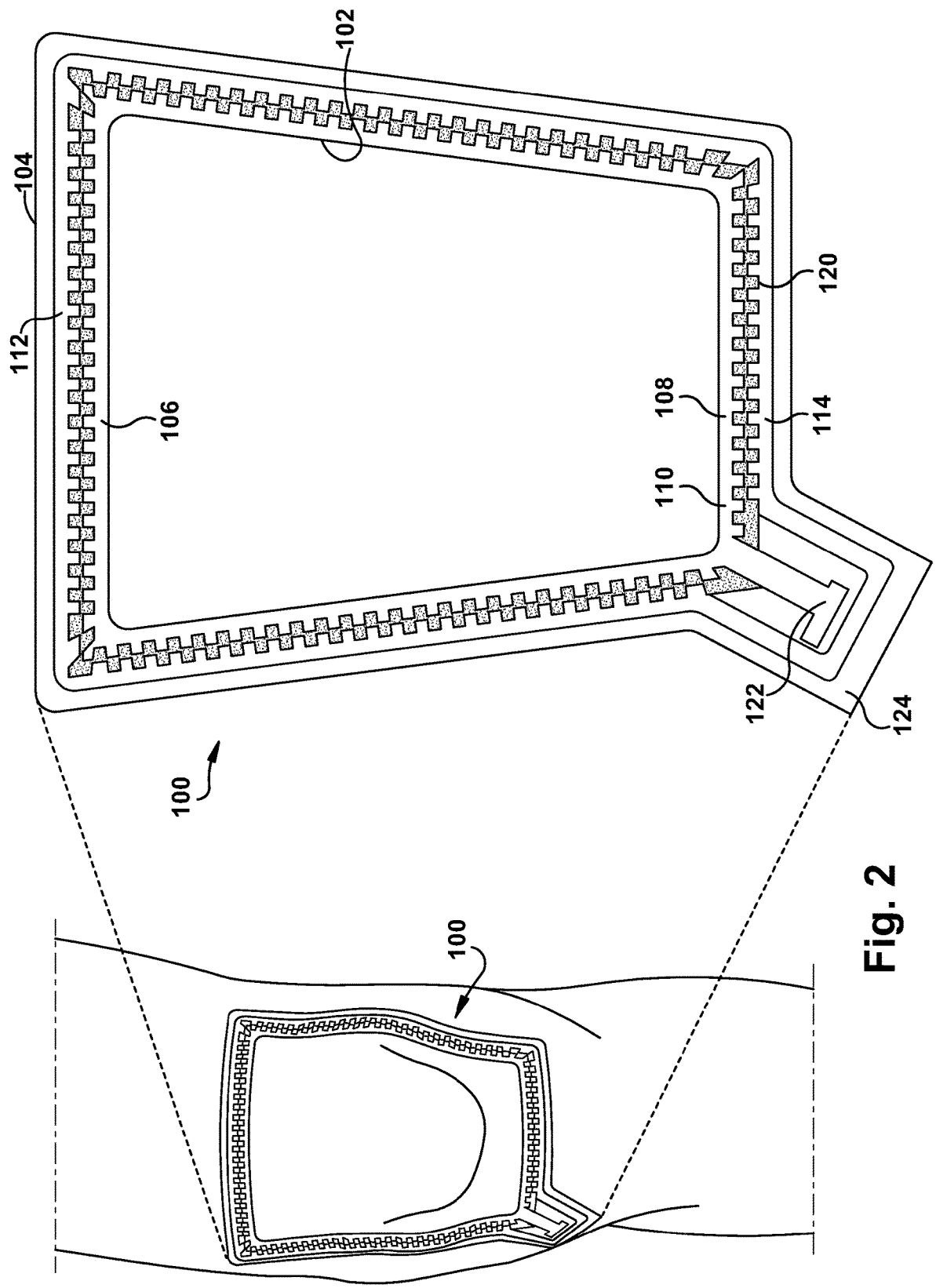
FIG. 2 is a plan view of a second embodiment of a self-regulating heater constructed in accordance with the present invention.

A heater 100 constructed in accordance with a second embodiment is illustrated in FIG. 2. The heater 100 is generally similar to the heater 10 illustrated in FIG. 1. The heater 100 is configured for placement on a body part of a patient. More specifically, the heater 100 is configured for placement around a joint, such as a knee, as shown. The heater 100 could also be placed around another joint, such as an elbow. The heater 100 has a central opening 102 into which the joint may extend. The heater 100 has a first layer or substrate 104, similar to the first layer 12 of FIG. 1, defining the opening 102. The first layer 104 may be relatively thin and flexible.

A second or electrically conductive layer 106, similar to the second layer 14 of FIG. 1, has a first inner bus 108 with a base 110. The base 110 of the first inner bus 108 extends around the opening 102. A second outer bus 112 of the conductive layer 106 has a base 114 extending around the base 110 of the first inner bus 108. The second outer bus 112 extends generally parallel to the first inner bus 108. The second bus 112 is spaced from the first bus 108. The first bus 108 may include finger portions extending toward the base 114 of the second bus 112. The second bus 112 may include finger portions extending toward the base 110 of the first bus 108. The heater 100 may have any desired shape such as a square, rectangle, triangle, pyramid, circle or oval.

A third or resistive layer 120 that experiences a PTC effect when heated, similar to the third layer 52 of FIG. 1, is connected to the conductive layer 106. The resistive layer 120 electrically connects the buses 108 and 112 of the second layer 106. The third layer 120 has a higher electrical resistance than the second layer 106. The resistive layer 120 generates heat when a voltage is applied across the buses 108, 112.

A fourth or interface layer (not shown), similar to the fourth layer 62 of FIG. 1, is connected to the resistive layer 120. The interface layer may be an adhesive that completely seals the heater 100. The interface layer may be used to attach the heater 100 directly to the skin of a patient, such as the skin around the knee. A first terminal (not shown) may be connected to an outwardly extending portion 122 of the first inner bus 108. A second terminal (not shown) may be connected to an outwardly extending portion 124 of the second outer bus 112. The outwardly extending portion 124 of the second outer bus 112 may extend around the outwardly extending portion 122 of the first bus 108. The first and second terminals may be connected to the buses 108, 112 in any desired manner, such as riveting or crimping. The terminals connect the heater 100 to a voltage supply.

Figure 3:
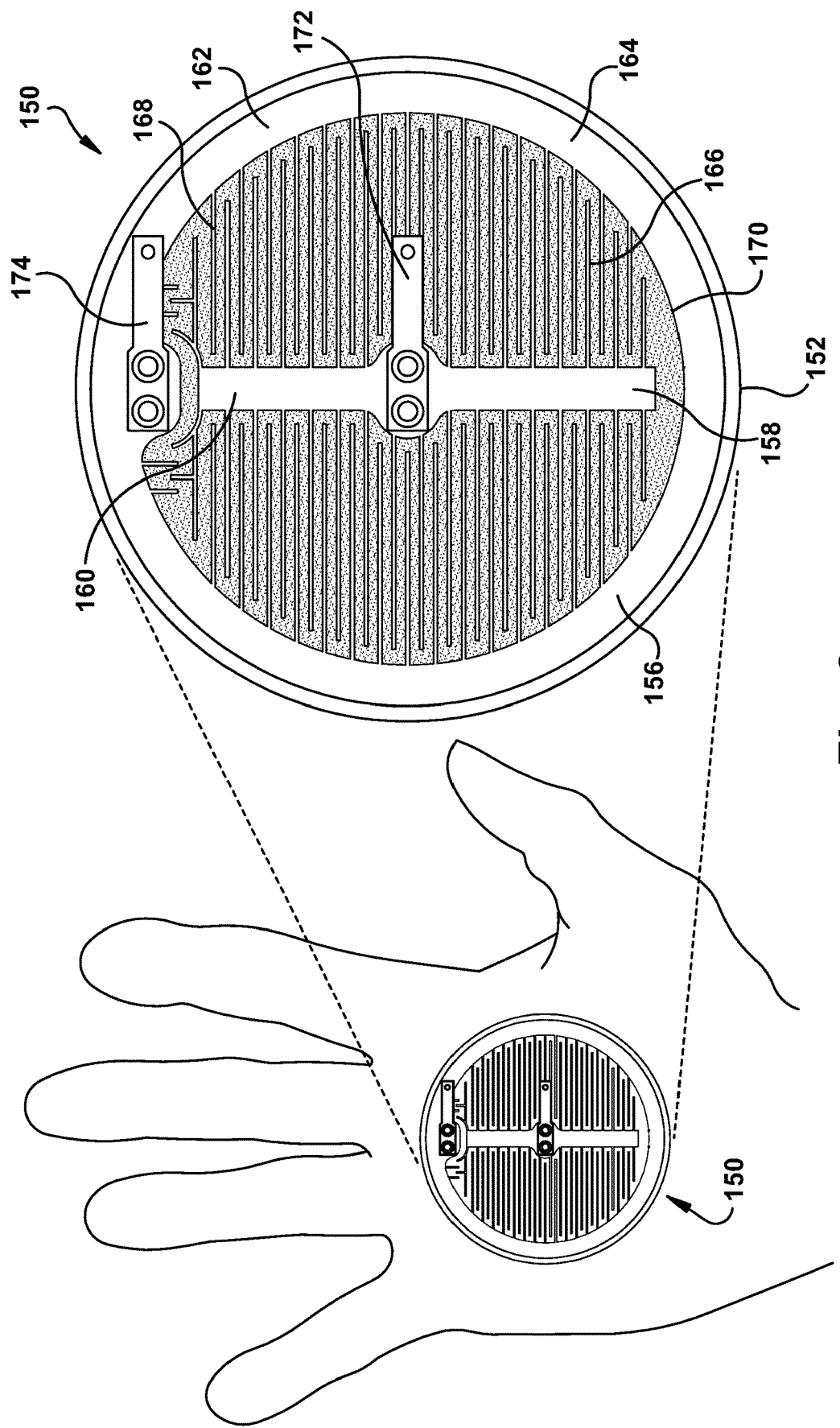
FIG. 3 is a plan view of a third embodiment of a self-regulating heater constructed in accordance with the present invention.

A heater 150 constructed in accordance with another embodiment is illustrated in FIG. 3. The heater 150 is generally similar to the heaters 10 and 100 illustrated in FIGS. 1 and 2. The heater 150 is configured for placement on the palm of a hand, as shown and has a circular shape. The heater 150 may be placed on any desired body part of a patient. The heater 150 has a first layer or substrate 152 defining the circular shape.

A second or electrically conductive layer 156 has a first inner bus 158 with a base 160. The base 160 of the first inner bus 158 extends along a diameter of the first layer 152. The base 160 has length that is less than the diameter of the circle. A second outer bus 162 of the conductive layer 156 has a base 164 extending adjacent the outer edge of the first layer 152 and around the first inner bus 158. The second outer bus 162 is spaced from the first bus 158. The first bus 158 may include finger portions 166 extending outwardly from the base 160 toward the base 164 of the second bus 162. The second bus 162 may include finger portions 168 extending inwardly toward the base 160 of the first bus 158. The finger portions 166, 168 may extend generally parallel to each other and perpendicular to the base 160 of the first bus 158. The heater 100 may have any desired shape such as a square, rectangle, triangle, pyramid, or oval.

A third or resistive layer 170 that experiences a PTC effect when heated is connected to the conductive layer 156. The resistive layer 170 electrically connects the busses 158 and 162 of the second layer 156. The second layer 156 has a lower electrical resistance than the resistive layer 170. The resistive layer 170 generates heat when a voltage is applied across the buses 158, 162.

A fourth or interface layer (not shown) is connected to the resistive layer 170. The interface layer may be an adhesive that completely seals the heater 150. The interface layer may be used to attach the heater 150 directly to the skin of a patient. A first terminal 172 may be connected to the first inner bus 158 and a second terminal 174 may be connected to the second outer bus 162. The first and second terminals may be connected to the busses 158, 162 in any desired manner, such as riveting or crimping. The terminals connect the heater 150 to a voltage supply.

Figure 4:
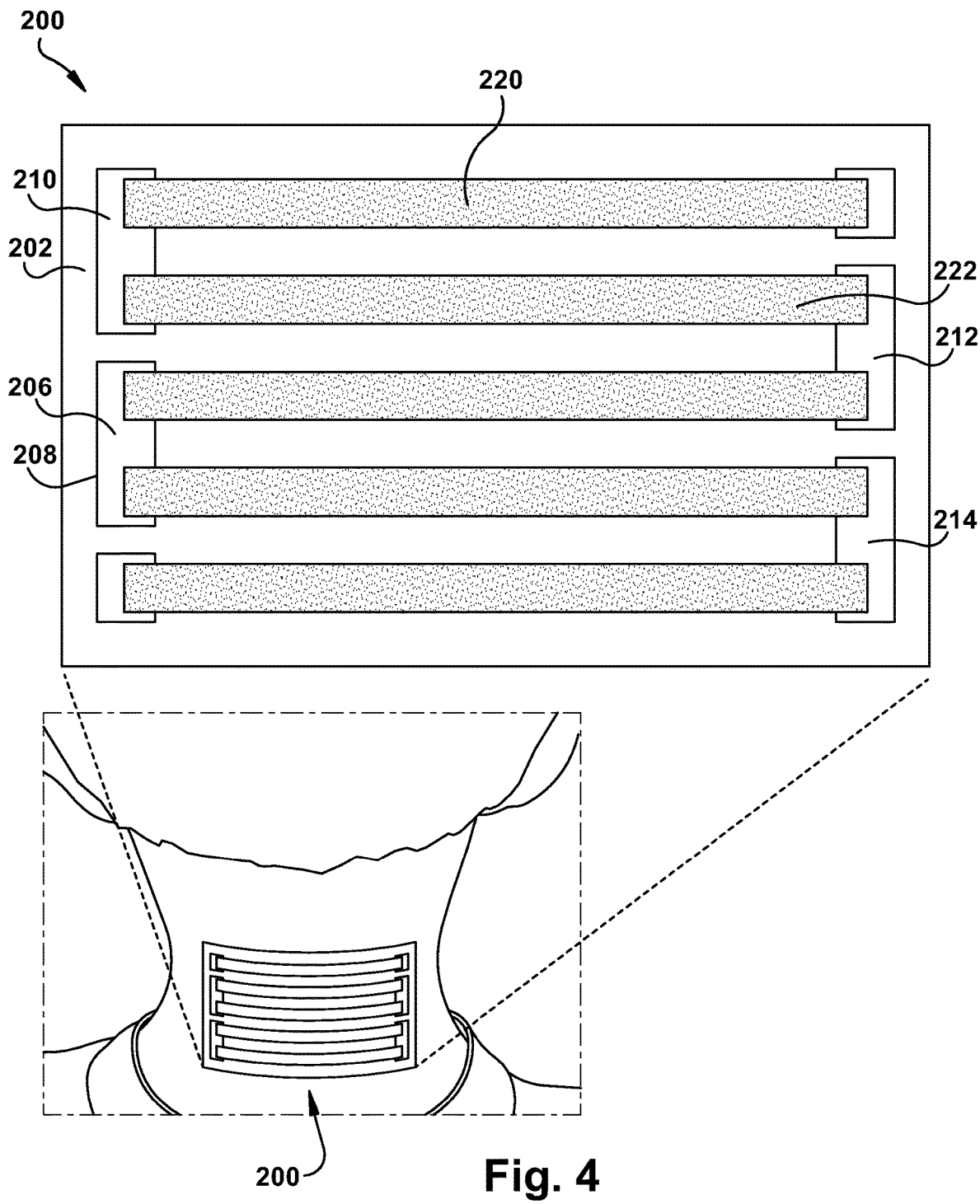
FIG. 4 is a plan view of a fourth embodiment of a self-regulating heater constructed in accordance with the present invention.

A heater 200 constructed in accordance with yet another embodiment is illustrated in FIG. 4. The heater 200 is generally similar to the heaters 10, 100 and 150 illustrated in FIGS. 1-3. The heater 200 is configured for placement on a neck of a patient and has a rectangular shape. The heater 200 may have any desired shape such as a square, triangle, pyramid, circle or oval. The heater 200 may be placed on a neck of a patient.

The heater 200 has a first layer or substrate 202 defining the rectangular shape. A second or electrically conductive layer 206 has a first bus 208 with a base 210. The base 210 of the first bus 208 extends along a first edge of the first layer 202. A second bus 212 of the conductive layer 206 has a base 214 extending along a second edge of the first layer 202. The second bus 212 extends generally parallel to the first bus 208 and is spaced from the first bus 208.

A third or resistive layer 220 that experiences a PTC effect when heated is connected to the conductive layer 202. The resistive layer 220 electrically connects the buses 208 and 212 of the second layer 206. The second layer 206 has a lower electrical resistance than the resistive layer 220. The resistive layer 220 generates heat when a voltage is applied across the buses 208, 212. The resistive layer 220 includes a plurality of strips 222 extending between the buses 208, 212. The strips 222 extend generally parallel to each other.

A skin interface layer (not shown) is connected to the resistive layer 220. The skin interface layer 220 may be an adhesive that completely seals the heater 200. The skin interface layer 220 may be used to attach the heater 200 directly to the skin of a patient. A first terminal (not shown) may be connected to the first bus 208 and a second terminal (not shown) may be connected to the second bus 212. The first and second terminals may be connected to the buses 208, 212 in any desired manner, such as riveting or crimping. The terminals connect the heater 200 to a voltage supply.

The heaters 10, 100, 150 and 200 have been described as having the conductive layer connected to the first or substrate layer and the resistive layer being connected to the conductive layer with the conductive layer between the first layer and the resistive layer. However, the resistive layer may engage and be connected to the first or substrate layer and the conductive layer connected to the resistive layer. If the resistive layer is connected to the first layer, the fourth layer may be directly connected to and engaging the conductive layer. Therefore, the fourth layer may engage and be connected to at least one of the conductive 14 and the resistive layer. Also, the heaters 10, 100, 150, and 200 have been described as being used for patient warming. It is contemplated that the heaters could be used as seat heaters for vehicles, floor mat heaters, floor heaters, or any other desired use.

From the above description of the invention, those skilled in the art will perceive improvements, changes and modifications. Such improvements, changes, and/or modifications within the skill of the art are intended to be covered by the appended claims.

Having described the invention, the following is claimed:

1. A self regulating heater comprising:
   a first layer made of an electrically insulating material, the first layer being thin and flexible;
   a second electrically conductive layer, the second layer including first and second buses spaced from each other;
   a third resistive layer electrically connecting the first and second buses, the third layer having a higher electrical resistance than the second layer, the third layer experiencing a positive temperature coefficient (PTC) effect when heated; and
   a fourth interface layer directly connected to at least one of the second electrically conductive layer and the third resistive layer;
   wherein the second electrically conductive layer runs along a perimeter of the heater,
   wherein the first bus has a base extending around the perimeter and the second bus has a base extending around the base of the first bus and the perimeter, and
   wherein the heater is configured for placement around a joint.

2. The self regulating heater of claim 1 wherein the second electrically:
   conductive layer is a screen printed flexible polymeric ink, the third resistive layer being
   screen printed on the second layer, the third resistive layer including a conductive carbon
   black filler material dispersed in a polymer having a crystalline structure, the fourth layer
   being an adhesive that completely seals the heater.

3. The self regulating heater of claim 1 wherein the fourth layer attaches the heater directly to skin of a patient.

4. The self regulating heater of claim 3 wherein the fourth layer is made of a hypoallergenic material.

5. The self regulating heater of claim 3 wherein the heater conforms to a body part of the patient when adhered directly to the skin of the patient.

6. The self regulating heater of claim 1 further including a first terminal connected to the first bus and a second terminal connected to the second bus, each of the first and second buses including finger portions, the finger portions having a width substantially smaller than the width of each of the bases.

7. The self regulating heater of claim 6 wherein a spacing between the fingers and the bases of the first and second buses varies across the heater.

8. The self regulating heater of claim 1 wherein the heater has at most a 4° F. difference across a surface of the heater.

9. The self regulating heater of claim 1 wherein the fourth layer is an adhesive that completely seals the heater, the fourth layer adhering the heater directly to skin of a patient, the heater conforming to a body part of the patient when adhered directly to the skin of the patient.

10. The self regulating heater of claim 1 wherein the heater only includes the first layer, the second conductive layer, the third resistive layer and the fourth interface layer.

11. The self regulating heater of claim 1 wherein the buses are parallel with each other.

12. The self regulating heater of claim 1 wherein the base of the first bus includes a first outwardly extending portion, and the base of the second bus includes a second outwardly extending portion extending around the first outwardly extending portion.

13. The self regulating heater of claim 1 wherein the third resistive layer is zigzag-shaped.

14. A self regulating heater comprising:
   a first layer made of an electrically insulating material, the first layer being thin and flexible;
   a second electrically conductive layer, the second layer including first and second buses spaced from each other;
   a third resistive layer electrically connecting the first and second buses, the third layer having a higher electrical resistance than the second layer, the third layer experiencing a positive temperature coefficient (PTC) effect when heated; and a fourth interface layer directly connected to at least one of the second electrically conductive layer and the third resistive layer;
   wherein the first layer defines a circular shape of the heater, a base of the first bus extends along a diameter of the first layer, a base of the second bus extending around an outer edge of the first layer and the first bus, and
   wherein the heater is configured for placement on a palm of a hand.

15. The self regulating heater of claim 14 wherein the first bus includes finger portions extending outwardly from the base of the first bus toward the base of the second bus, the second bus including finger portions extending inwardly toward the base of the first bus, the finger portions of the first and second buses extending generally parallel to each other and perpendicular to the base of the first bus.

* * * * *